(12) United States Patent
Ondrla et al.

(10) Patent No.: US 8,419,798 B2
(45) Date of Patent: Apr. 16, 2013

(54) JOINT PROSTHESIS WITH INFINITELY POSITIONABLE HEAD

(75) Inventors: Jeff Ondrla, Leesburg, IN (US); Gerald Ross Williams, Jr., Villanova, PA (US); Joseph Patrick Iannotti, Solon, OH (US); Paul Gibbons, Yorks (GB); James Edward Clark, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/748,448

(22) Filed: Dec. 30, 2003

(65) Prior Publication Data
US 2005/0143829 A1 Jun. 30, 2005

(51) Int. Cl.
*A61F 2/40* (2006.01)

(52) U.S. Cl.
USPC ................ 623/19.12; 623/19.14; 623/22.45

(58) Field of Classification Search ........... 623/19.11, 623/19.12, 19.13, 19.14, 22.45, 22.46, 23.42
See application file for complete search history.

(56) References Cited

U.S. PATENT DOCUMENTS

| | | | |
|---|---|---|---|
| 4,003,095 A | 1/1977 | Gristina | |
| 4,822,370 A | 4/1989 | Schelhas | |
| 5,076,541 A | 12/1991 | Daghe et al. | |
| 5,080,685 A | 1/1992 | Bolesky et al. | |
| 5,314,479 A | 5/1994 | Rockwood, Jr. et al. | |
| 5,358,526 A | 10/1994 | Tornier | |
| 5,370,706 A | 12/1994 | Bolesky et al. | |
| 5,702,457 A | 12/1997 | Walch et al. | |
| 5,725,597 A | 3/1998 | Hwang et al. | |
| 5,741,335 A | 4/1998 | Gerber et al. | |
| 5,743,898 A | 4/1998 | Bailey et al. | |
| 5,910,143 A | 6/1999 | Cripe et al. | |
| 6,197,062 B1 | 3/2001 | Fenlin | |
| 6,203,575 B1 | 3/2001 | Farey | |
| 6,206,925 B1 | 3/2001 | Tornier | |
| 6,228,120 B1 | 5/2001 | Leonard et al. | |
| 6,283,999 B1 | 9/2001 | Rockwood, Jr. | |
| 6,328,748 B1 | 12/2001 | Hennig | |
| 6,361,566 B1 | 3/2002 | Al-Hafez | |
| 6,478,500 B1 | 11/2002 | Farenholtz | |
| 6,558,425 B2 | 5/2003 | Rockwood, Jr. | |
| 6,620,197 B2 | 9/2003 | Maroney et al. | |

(Continued)

FOREIGN PATENT DOCUMENTS

| DE | 44 45 892 | 6/1996 |
|---|---|---|
| DE | 19509037 C1 | 9/1996 |

(Continued)

OTHER PUBLICATIONS

Australian Search Report in Australian application AU2005247033, mailed Apr. 23, 2010 (2 pages).

(Continued)

*Primary Examiner* — David H Willse
*Assistant Examiner* — Javier Blanco
(74) *Attorney, Agent, or Firm* — Maginot, Moore & Beck, LLP

(57) ABSTRACT

A joint prosthesis includes a head component that is engaged to a bone stem through a mounting element. The mounting element is configured for articulating engagement with the stem to permit angular positioning of the head component in multiple degrees of freedom. The mounting element is fastened to the stem by a press-fit engagement and a separate mechanical fastener.

15 Claims, 2 Drawing Sheets

U.S. PATENT DOCUMENTS

| | | |
|---|---|---|
| 6,626,946 B1 | 9/2003 | Walch et al. |
| 6,673,114 B2 | 1/2004 | Hartdegen et al. |
| 6,736,851 B2 | 5/2004 | Maroney et al. |
| 6,736,852 B2 | 5/2004 | Callaway et al. |
| 6,749,637 B1 | 6/2004 | Bahler |
| 6,776,799 B2 | 8/2004 | Ball et al. |
| 6,953,478 B2 | 10/2005 | Bouttens et al. |
| 7,192,449 B1 | 3/2007 | McQueen et al. |
| 7,238,207 B2 | 7/2007 | Blatter et al. |
| 7,431,736 B2 | 10/2008 | Maroney et al. |
| 2001/0041940 A1 | 11/2001 | Pearl |
| 2001/0053935 A1 | 12/2001 | Hartdegen et al. |
| 2002/0016634 A1 | 2/2002 | Maroney et al. |
| 2003/0014112 A1 | 1/2003 | Ralph et al. |
| 2003/0040802 A1 | 2/2003 | Errico et al. |
| 2003/0097183 A1 | 5/2003 | Rauscher et al. |
| 2004/0002765 A1 | 1/2004 | Maroney et al. |
| 2004/0010261 A1 | 1/2004 | Hoag et al. |
| 2004/0030400 A1 | 2/2004 | Horber |
| 2004/0064142 A1 | 4/2004 | Ball et al. |
| 2004/0064188 A1 | 4/2004 | Ball et al. |
| 2004/0064189 A1 | 4/2004 | Maroney et al. |
| 2004/0122440 A1 | 6/2004 | Daniels et al. |
| 2004/0167629 A1 | 8/2004 | Geremakis et al. |
| 2005/0113931 A1 | 5/2005 | Horber |
| 2005/0143829 A1 | 6/2005 | Ondrla et al. |
| 2005/0149050 A1 | 7/2005 | Stifter et al. |
| 2005/0187637 A1 | 8/2005 | Karrer et al. |
| 2005/0251263 A1 | 11/2005 | Forrer et al. |
| 2005/0288681 A1 | 12/2005 | Klotz et al. |
| 2006/0142872 A1 | 6/2006 | Klotz et al. |
| 2007/0078519 A1 | 4/2007 | Klotz |
| 2007/0112430 A1 | 5/2007 | Simmen et al. |

FOREIGN PATENT DOCUMENTS

| | | |
|---|---|---|
| DE | 199 51 141 | 5/2001 |
| DE | 101 23 517 | 11/2002 |
| DE | 202005020876 U1 | 10/2006 |
| EP | 0549480 A1 | 6/1993 |
| EP | 0679375 A1 | 11/1995 |
| EP | 0712617 A1 | 5/1996 |
| EP | 0715836 A1 | 6/1996 |
| EP | 0931522 A1 | 7/1999 |
| EP | 1186278 A2 | 3/2002 |
| EP | 1314407 A1 | 5/2003 |
| EP | 1321114 A1 | 6/2003 |
| EP | 1393697 A1 | 3/2004 |
| EP | 1402856 A1 | 3/2004 |
| EP | 1769776 A1 | 7/2004 |
| EP | 1681037 A2 | 7/2006 |
| FR | 2731612 A1 | 9/1996 |
| JP | 2004512922 A | 4/2004 |
| WO | 9303688 A1 | 3/1993 |
| WO | WO 0122905 A1 * | 4/2001 |
| WO | WO 0239932 A1 * | 5/2002 |
| WO | 03096870 A2 | 11/2003 |
| WO | WO 03096939 A1 * | 11/2003 |

OTHER PUBLICATIONS

Australian Search Report in Australian application AU2005246996, mailed Apr. 27, 2010 (3 pages.).

Australian Search Report in Australian application AU2006225167, mailed Mar. 22, 2011 (2 pages).

European Search Report in European application EP05257963.8, mailed Dec. 20, 2007 (5 pages).

European Search Report in European application EP05257964.6, mailed Dec. 20, 2007 (8 pages).

European Search Report in European application EP06255073.6, mailed Jan. 5, 2007 (8 pages).

European Search Report in European application EP09162325.6, mailed Oct. 2, 2009 (6 pages).

European Search Report in European application EP10178881.8, mailed Mar. 10, 2011 (5 pages).

European Search Report in European application EP10178895.8, mailed Dec. 14, 2010 (7 pages).

Japanese Office Action in Japanese application JP2005-378997, mailed Feb. 9, 2010 (12 pages including translation).

Japanese Office Action in Japanese application JP2006-267228, mailed Oct. 5, 2010 (4 pages).

The McElroy Translation Company, English translation of German Patent No. DE 101 23 517 C1, dated Jan. 2006 (20 pages).

* cited by examiner

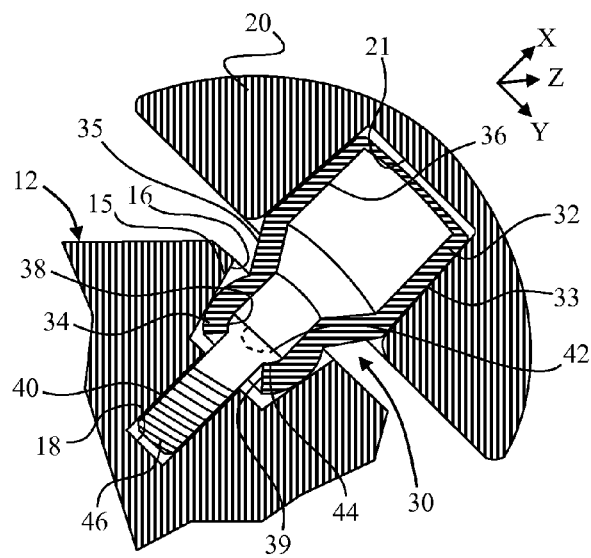
FIG. 2
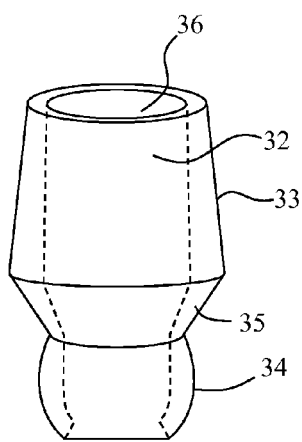
FIG. 3
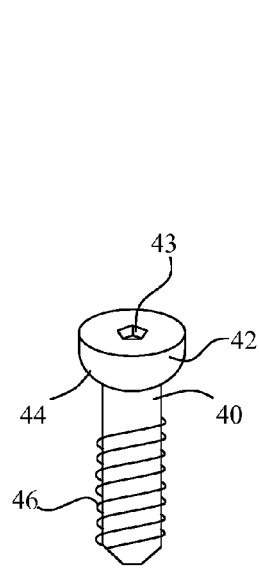
FIG. 4
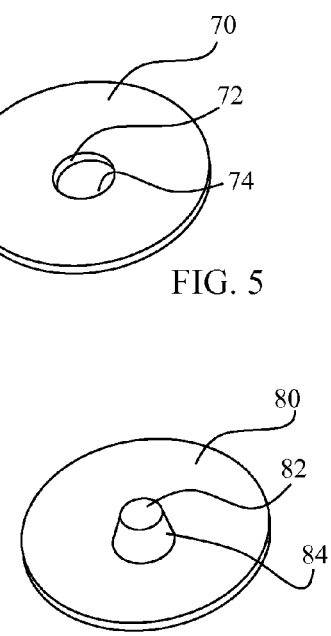
FIG. 5
FIG. 6
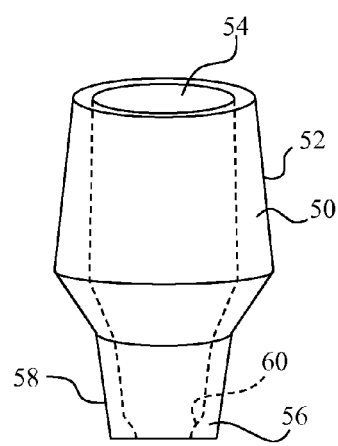
FIG. 7

JOINT PROSTHESIS WITH INFINITELY POSITIONABLE HEAD

BACKGROUND OF THE INVENTION

The present invention relates to joint prosthesis, and particularly to prosthesis having an articulating head component. More specifically, the invention relates to a system for achieving infinitely variable positions for the head component relative to a bone engaging portion of the prosthesis.

Repair and replacement of human joints, such as the knee, shoulder, elbow and hip, has become a more and more frequent medical treatment. Longer life spans mean that the joints endure more wear and tear. More sports activities mean greater likelihood of serious joint injuries. Treatment of injuries, wear and disease in human joints has progressed from the use of orthotics to mask the problem, to fusion of the joint, to the use of prostheses to replace the damaged joint component(s).

As the success rate for total or partial joint replacements has increased, so too has the need for modularity and universality in the joint prosthesis. Patient variety means that no single size or configuration of joint prosthesis will suffice. The physical dimensions of a patient's joint components vary, as well as the bio-mechanic relationship between these components. For instance, in a shoulder prosthesis, the relationship between the articulating humeral and glenoid components can be significantly different between patients. These relationships are especially important where only one component of the joint is being replaced and must integrate with the existing natural opposing joint component.

For instance, in many shoulder surgeries, only the humeral component is replaced, leaving the glenoid component intact. In this case, it is imperative that the articulating surface of the humeral component match the articulating surface of the glenoid component as perfectly as possible, both statically and dynamically. With a typical humeral prosthesis, version and inclination are adjusted by the geometry of the head of the prosthesis. In other words, certain pre-determined head geometries are available that can be selected for a mating glenoid component. Absent an infinite variety of pre-determined head geometries, the resulting humeral prosthesis can often only achieve a best-fit relationship to the glenoid component of the shoulder joint.

In a typical surgical procedure, a trial component will be used to determine the optimum final component to be fixed to the bone. In most cases, the surgeon is able to make a good selection that fits the joint very well. However, in some cases, the accuracy of the fit cannot be determined until the surgery is completed and the patient has had an opportunity to exercise the repaired joint. Where significantly problems arise, a revision surgery may be necessary to replace an improperly sized or configured joint component. One typical revision surgery requires removal of the entire prosthesis from the bone and replacement with a different prosthesis.

There is a significant need for a joint prosthesis that is both modular and universal. Such a prosthesis would be easily manipulated during the surgery and capable of achieving nearly infinite version and inclination angles. Moreover, an optimum prosthesis would be readily available for modification in a revision surgery without having to remove the entire prosthesis.

SUMMARY OF THE INVENTION

These and other needs of the prior art are met by the present invention in which a joint component is itself mounted to a bone engaging component of a prosthesis by an articulating mounting element. The articulating mounting element allows the joint component to adopt an infinitely variable range of angles in three dimensions relative to the bone engaging component.

In a preferred embodiment, the prosthesis is a humeral prosthesis for a shoulder replacement procedure. The humeral prosthesis includes a stem configured for engagement within the radius bone. The stem defines a tapered bore facing the glenoid component of the shoulder joint. A distal portion of the mounting element is configured to be initially mobile within the bore, while a proximal end is configured to carry the humeral joint component or trial. The mounting element can be articulated to find the optimum position for the humeral joint component. The mounting element can then be temporarily tightened to hold the humeral joint component in position to verify the version and inclination angles of the component. The mounting element can be finally tightened to complete the humeral prosthesis.

In one aspect of the invention, the mounting element is tightened by two mechanisms. In the first, the mounting element achieves a friction fit with the tapered bore. The second fixation mechanism includes a screw that is threaded into a threaded bore portion of the tapered bore in the stem. The screw bears against the mounting element to lock the element in position within the tapered bore. In accordance with a preferred embodiment of the invention, screw is internal to the mounting element and the proximal portion of the element provides a passageway to introduce and tighten the screw in situ.

The proximal portion of the mounting element defines a tapered surface that mates with a tapered feature of a head component for the humeral prosthesis. The head component can include an opening to access the passageway in the proximal portion of the mounting element, thereby providing access to the fixation screw.

The present invention contemplates a fully modular joint prosthesis. Thus, a number of joint components can be provided for interchangeable use to construct the prosthesis. For instance, a fixed mounting element can replace the articulating mounting element. Similarly, the head component for the joint prosthesis can be configured to mate directly with the stem, with the fixed mounting element or the articulating mounting element. The head component can also be modified to close the end of the passageway in the proximal portion of the articulating mounting element.

It is one object of the invention to provide a joint prosthesis that is both modular and universal. This object is achieved by features that permit infinitely variable positioning of a mating joint component relative to a bone engaging portion of the prosthesis.

Another object is to provide a prosthesis that is readily available for modification, whether during initial implantation or during a subsequent revision procedure. A further object of the invention is to combine these features without creating a profile or prominence greater than is achieved by current joint prostheses.

These objects and particular benefits of the invention will be appreciated upon consideration of the following written description together with the accompanying figures.

DESCRIPTION OF THE FIGURES

FIG. 2 is an enlarged cross-sectional view of a portion of a joint prosthesis in accordance with one embodiment of the invention.

FIG. 3 is a front view of an articulating mounting element used with the joint prosthesis shown in FIG. 2.

FIG. 4 is a front view of a fixation screw used with the joint prosthesis depicted in FIG. 2.

FIG. 5 is a bottom view of a head component of the joint prosthesis illustrated in FIG. 2.

FIG. 6 is a bottom view of an alternative head component for use with the joint prosthesis shown in FIG. 2.

FIG. 7 is a front view of an alternative mounting element that can substitute for the articulating mounting element in the joint prosthesis of FIG. 2.

DESCRIPTION OF THE PREFERRED EMBODIMENTS

Figure 1:
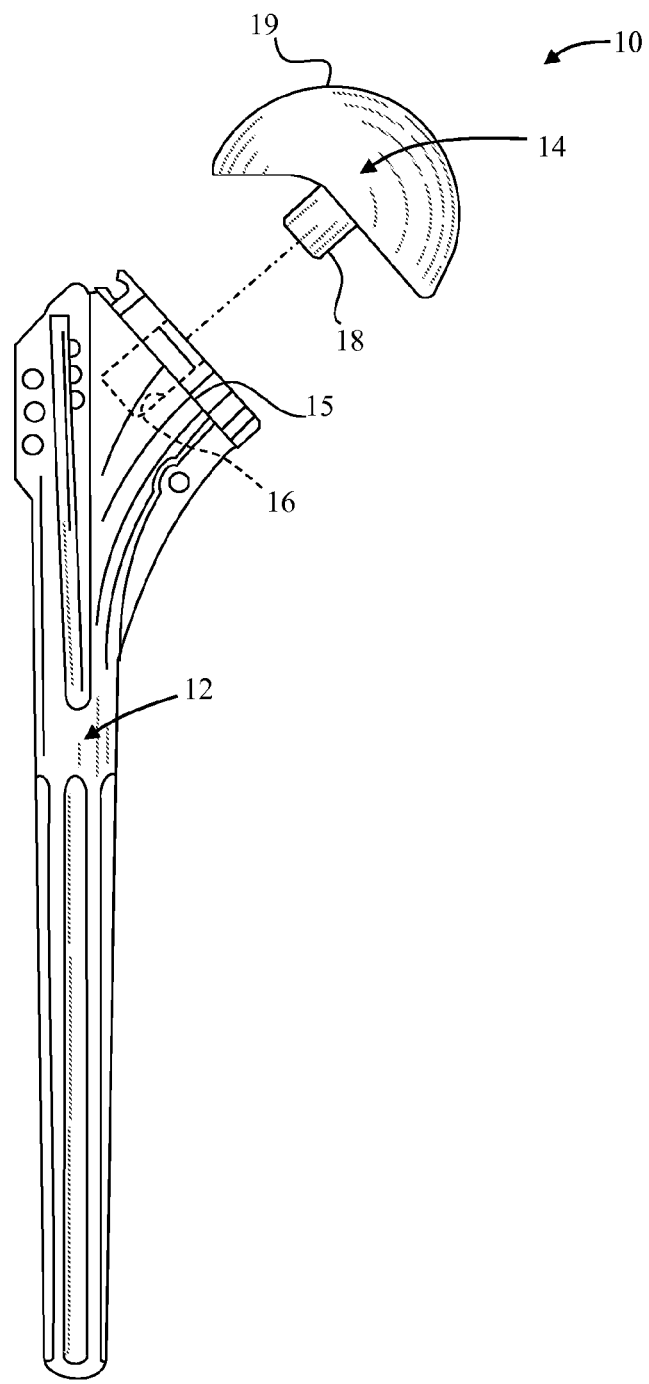
FIG. 1 is a side view of a prior art humeral prosthesis.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

A typical joint prosthesis of the prior art is illustrated in FIG. 1. The prosthesis 10 is the humeral component of a shoulder prosthesis that can be implanted in the humerus bone for articulating engagement with the natural glenoid or with a glenoid prosthesis. The prosthesis 10 includes a stem 12 configured to be implanted within the humerus bone in a conventional manner. The stem 12 forms a platform surface 15 that faces the glenoid component of the joint when the prosthesis is in its operative position. The platform surface 15 defines a tapered bore for use in mounting the articulating head component 14. The head component includes a tapered post 18 that can be press-fit or friction-fit within the tapered bore 16 to firmly mount the head component to the stem 12.

The prosthesis 10 can be a modular prosthesis, meaning that a number of stem and head geometries can be provided from which a selection can be made that most closely approximates the natural joint components of the patient. Thus the angle of the platform surface 15 can be different among stems 12. While all head components 14 will include a generally spherical bearing surface 19, the orientation of this surface relative to the platform surface 15 can be changed. Specifically, the location of the post 18 relative to the bearing surface 19 can be offset from the center of the surface (i.e., an eccentric head). In some cases, the angle of the post can be different between head components 14.

This modularity feature is improved by the present invention that introduces an articulating mounting element 30 between the stem 12 and a head component 20, as shown in FIGS. 2-4. In one embodiment of the invention, the mounting element 30 includes a proximal portion 33 that mates with the head component 20. In a specific embodiment, the proximal portion 33 defines a tapered surface that is press-fit or friction-fit within a complementary bore 21 defined in the head component.

The mounting element 30 further includes an articulating portion 34 that can be preferably in the form of a spherical ball joint. The articulating portion is sized to achieve a press-fit engagement within the tapered bore 16 of the stem 12 when the portion 34 is pushed sufficiently far into the bore. The spherical shape of the articulating portion 34 allows the mounting element 30 to rotate about three dimensional axes x, y, z. Thus, the mounting element can rotate about its own axis (the x axis), pivot about a version axis (the y axis) or pivot about an inclination axis (the z axis). The mounting element 30 can rotate a full 360° about its own axis. However, the pivot range in the other two degrees of freedom is limited by contact between the articulating mounting element or the head component and the platform surface 15 of the stem 12. The range of motion in these two degrees of freedom are maximized by the intermediate portion 35 connecting the articulating portion to the proximal portion. In particular, the intermediate portion 35 can be angled away from the articulating portion 34 to provide clearance as the mounting element is pivoted.

In one feature of the present invention, a second fixation capability is provided to augment the friction or press-fit between the articulating portion 34 and the tapered bore 16. In particular, a machine screw 40 is provided that includes a threaded portion 46 configured to mate with a threaded bore 18 in the stem 12. The bore 18 is concentrically disposed at the base of the tapered bore 16. The screw 40 is introduced into the threaded bore 18 through the articulating mounting element 30.

As shown in FIG. 2, the mounting element 30 defines a central passageway 36 that extends through the length of element and that is open at its proximal and distal ends. The passageway defines an internal bearing surface 38 at the distal end of the element, or more specifically at the base of the articulating portion 34. The screw includes a head 42 that includes an underside surface 44 that is complementary with the internal bearing surface. These two surfaces form a spherical bearing interface that allows the mounting element 30 to experience its full range of angular motion without interference from the screw 40, even when the screw is loosely threaded into the threaded bore 18. The articulating portion 34 defines a relief 39 at the distal end of the passageway 36 to facilitate this full range of movement of the mounting element.

The passageway 36 in the mounting element allows introduction of the screw 40 through the mounting element and into the threaded bore 18. The screw can be loosely threaded into the bore to permit movement of the mounting element. Once the proper position for the mounting element 30 has been achieved, the screw can be tightened using a tool engaged within the tool recess 43 on the head 42 of the screw. As the screw is tightened, it drives the articulating portion 34 deeper into the angled bore 16, thereby fixing the mounting element against further articulation. The screw thus combines with the friction or press-fit feature to lock the construct.

It is contemplated that the articulating mounting element 30 can be utilized with the stem 12 engaged within the bone, such as the humerus. In order to determine the proper configuration for the joint prosthesis, a head component, such as component 20 is carried by the proximal portion 32 of the mounting element. As can be seen in FIG. 2, the head component 20 is closed over the passageway 36, thereby preventing access to the screw 40 unless the head portion is removed. In one embodiment, a head component 70 can be provided as depicted in FIG. 5. This head component 70 includes a tapered bore 72 that is configured for mating engagement with the proximal portion 32. However, unlike the head component 20, the bore 72 includes an opening 74 at the proximal face of the component. Thus, the opening 74 provides complete access to the screw 40, even when the head component 70 is mounted on the mounting element 30.

In using the mounting element 30 of the present invention, the element 30 can be initially mated with a head component 70. The component can be a final component or a trial. In the preferred embodiment, the two components mate by way of a socket taper as is known in the art. The mounting element 30, with the head component mounted thereon, can be maneuvered to position the articulating portion 34 within the tapered bore 16. The screw 40 can be introduced through the opening 74 and along the passageway 36 so that the screw can be threaded into the threaded bore 18 in the stem 12.

The screw 40 can be loosely tightened so that the articulating portion 34 can rotate, but the screw head 42 offers some resistance to help hold the head component in position. The head component 70 can be manipulated as necessary to achieve an angular orientation that will mate efficiently with the opposite component of the joint (the glenoid component in the case of a shoulder prosthesis). The screw 40 can be tightened and loosened as necessary to hold the head component in position to verify proper mating fit between the joint components.

If it is determined that a different head component is needed, the component can be removed from the mounting element 34 without disturbing the position of the mounting element relative to the stem 12. Once the proper head component has been selected and situated at its optimum orientation, the screw 40 can be fully tightened into the bore 18.

The present invention contemplates a modular system that can accommodate a wide range of joint constructs. For instance, a head component 80 can be provided as shown in FIG. 6. This head component includes a mounting post 82 with a tapered engagement surface 84 that is configured to be mounted directly within the tapered bore 16. The head component 80 can be used where no angular variations are required.

The head component 80 can also be press-fit into the passageway 36 of the mounting element 30. In this case, the passageway is formed as a tapered bore, similar to the bore 16 in the stem 12. With this specific embodiment, the post 82 can define a bore therethrough that communicates with the passageway 36 in the mounting element to permit introduction of the screw 40 therethrough.

A further component of the modular system is the fixed mounting element 50 shown in FIG. 7. This fixed element includes a mounting portion 56 having a tapered surface 58 configured for press or friction-fit engagement with the tapered bore 16. The proximal portion 50 can have a tapered surface 52 for engagement within the bore 21 of the head component 20 (FIG. 2), or within the bore 72 of the head component 70 (FIG. 5). As is apparent from FIG. 7, the mounting element 50 does not accommodate changes in version or inclination angle, the degrees of freedom of movement of the element being limited to the longitudinal axis of the element.

The mounting element 50 can include a bore 54 that can be tapered to receive the post 82 of the head portion 80 (FIG. 6). In addition, the bore can provide a passageway for introduction of a mounting screw, like the screw 40 depicted in FIG. 4. The bore can form a bearing surface 60 against which the surface 44 of the screw 40 bears to clamp the mounting element 50 to the stem 12.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

For instance, while the illustrated embodiments relate to a humeral component of a shoulder prosthesis, the connection element of the present invention can be utilized in other joints to engage a joint component to a bone engaging component of the prosthesis.

The preferred embodiment includes a machine screw 40 for final securement of the mounting element 30 to the stem by way of the mating threaded bore 18. Other forms of mechanical fastener are contemplated that can effect final fixation of the mounting element to the stem. For instance, a press-fit pin can be provided that is pressed into a complementary bore (in lieu of the threaded bore 18). The pin would retain the configuration of the head 42 of the screw 40, most particularly the spherical underside surface 44 and would operate to press the articulating portion 34 into the tapered bore 16.

Furthermore, while the preferred embodiment contemplates angular adjustment capabilities in all degrees of freedom, the mounting element can be configured to limit angular movement to specific directions. For instance, instead of a spherical interface, the articulating portion 34 can include a flat side opposing a corresponding flat side to the bore 16 such that rotation of the portion 34 between the two flat sides if prohibited.

What is claimed is:

1. A shoulder prosthesis comprising:
   a stem configured to be implanted within a bone, the stem defining a first coupler bore;
   a joint component having a bearing surface and defining a second coupler bore; and
   a mounting element having (i) a proximal portion received within the second coupler bore of the joint component in a friction fit manner, and (ii) a spherical articulating portion received within the first coupler bore of the stem, wherein:
   the stem includes a proximal surface that defines a coupler opening through which the mounting element extends, and the stem, when viewed in a cross-section, further includes an interior wall portion located within the first coupler bore that extends inwardly toward a longitudinal axis of the first coupler bore from the proximal surface in a straight line;
   the spherical articulating portion of the mounting element touches the interior wall portion at a point along the straight line;
   the mounting element defines a passageway extending therethough; and
   a proximal part of a fastener is located within the passageway, and a distal part of the fastener contacts the stem.

2. The prosthesis of claim 1, wherein the second coupler bore of the joint component defines a female taper component, and the proximal portion of the mounting element defines a male taper component configured to mate with the female taper component.

3. The prosthesis of claim 1, wherein the stem is configured to be implanted within a humerus.

4. The prosthesis of claim 1, wherein the bearing surface of the joint component is configured to mate with a glenoid component.

5. A shoulder prosthesis comprising:
   a stem configured to be implanted within a bone, the stem including an internal bore;
   a joint component having a bearing surface;
   a mounting element configured for engagement with the joint component and having a spherical articulating portion received within the internal bore of the stem, the spherical articulating portion configured for press-fit engagement with the internal bore such that the spherical articulating portion touches the internal bore around substantially an entire perimeter of the bore defined by the intersection of a plane with the internal bore; and a fastener having a first portion coupled with the spherical articulating portion of the mounting element and a second portion directly coupled with the stem.

6. The prosthesis of claim 5, wherein the mounting element comprises an internal bore and the fastener extends within the internal bore of the mounting element.

7. The prosthesis of claim 5, wherein the internal bore comprises a tapered portion, and the perimeter of the bore is defined by the intersection of the plane with the tapered portion of the bore.

8. The prosthesis of claim 7, wherein the tapered portion extends from an external surface portion of the stem.

9. The prosthesis of claim 8, wherein the internal bore further comprises a threaded portion and the fastener is threadingly engaged with the threaded portion of the internal bore.

10. The prosthesis of claim 9, wherein the mounting element further comprises a bearing portion within a cavity and the fastener is configured to bear upon the bearing portion.

11. A shoulder prosthesis comprising:

a stem configured to be implanted within a bone, the stem defining a first coupler bore;

a joint component having a bearing surface and defining a second coupler bore; and a mounting element having (i) a proximal portion received within the second coupler bore of the joint component in a friction fit manner, and (ii) a spherical articulating portion received within the first coupler bore of the stem, wherein:

the stem includes a proximal surface that defines a coupler opening through which the mounting element extends, and the stem, when viewed in a cross-section, further includes an interior wall portion located within the first coupler bore that extends inwardly toward a longitudinal axis of the first coupler bore from the proximal surface in a straight line;

the spherical articulating portion of the mounting element touches the interior wall portion at a point along the straight line between a proximal portion of the straight line and a distal portion of the straight line.

12. The prosthesis of claim 11, wherein:

the mounting element defines a passageway extending therethough; and a proximal part of a fastener is located within the passageway, and a distal part of the fastener contacts the stem.

13. The prosthesis of claim 11, wherein the second coupler bore of the joint component defines a female taper component, and the proximal portion of the mounting element defines a male taper component configured to mate with the female taper component.

14. The prosthesis of claim 11, wherein the stem is configured to be implanted within a humerus.

15. The prosthesis of claim 11, wherein the bearing surface of the joint component is configured to mate with a glenoid component.

* * * * *